(12) United States Patent
Seefried

(10) Patent No.: US 9,638,651 B2
(45) Date of Patent: May 2, 2017

(54) METHOD AND CIRCUIT FOR EVALUATING A PHYSICAL QUANTITY DETECTED BY A SENSOR

(71) Applicant: Pepperl + Fuchs GmbH, Mannheim (DE)

(72) Inventor: Roland Seefried, Heidelberg (DE)

(73) Assignee: Pepperl + Fuchs GmbH (DE)

( * ) Notice: Subject to any disclaimer, the term of this patent is extended or adjusted under 35 U.S.C. 154(b) by 85 days.

(21) Appl. No.: 14/627,245

(22) Filed: Feb. 20, 2015

(65) Prior Publication Data

US 2015/0233853 A1    Aug. 20, 2015

(30) Foreign Application Priority Data

Feb. 20, 2014 (EP) ...................................... 14155957

(51) Int. Cl.
*G01N 27/02* (2006.01)
(52) U.S. Cl.
CPC .................................. *G01N 27/025* (2013.01)
(58) Field of Classification Search
None
See application file for complete search history.

(56) References Cited

U.S. PATENT DOCUMENTS

| | | | | |
|---|---|---|---|---|
| 6,215,365 B1* | 4/2001 | Kurkovskiy | ........... | H03K 3/014 324/236 |
| 2006/0061423 A1* | 3/2006 | Wang | ................... | H03K 5/1565 331/16 |
| 2008/0298784 A1* | 12/2008 | Kastner | ..................... | G01P 3/44 388/811 |

FOREIGN PATENT DOCUMENTS

| | | |
|---|---|---|
| DE | 102004034190 A1 | 2/2006 |
| EP | 0537747 A2 | 4/1993 |
| WO | WO-00-76070 A1 | 12/2000 |

* cited by examiner

*Primary Examiner* — Jermele M Hollington
*Assistant Examiner* — Douglas X Rodriguez
(74) *Attorney, Agent, or Firm* — Harness, Dickey & Pierce, P.L.C.

(57) ABSTRACT

A method for measuring a physical quantity with a, particularly inductive, sensor element and for providing a sensor output depending on the physical quantity. The sensor element is part of a resonant circuit whose attenuation depends on the physical quantity being measured. The resonant circuit is excited to generate a periodic oscillation signal, the amplitude of which depends on the attenuation. The oscillation signal is compared with a comparator threshold value in a comparator to produce a periodic comparator signal with a duty cycle depending on the comparator threshold value. The comparator threshold value is set to be different from a mean value of the oscillation signal so that a duty cycle different from 50% is achieved. The sensor output is output depending on the duty cycle of the comparator signal.

14 Claims, 4 Drawing Sheets

METHOD AND CIRCUIT FOR EVALUATING A PHYSICAL QUANTITY DETECTED BY A SENSOR

CROSS-REFERENCE TO RELATED APPLICATIONS

This application claims the benefit and priority of European Patent Application No. 14155957.5 filed on Feb. 20, 2014, the entire disclosure of which is incorporated by reference herein.

BACKGROUND

This section provides background information related to the present disclosure which is not necessarily prior art.

TECHNICAL FIELD

The present invention generally relates to sensors, particularly sensors for use in an oscillator, wherein an oscillation signal depending on a physical quantity is provided. Furthermore, the present invention relates to possibilities for evaluating an oscillating signal influenced by a sensor element to obtain a sensor output.

DISCUSSION

Inductive and capacitive sensor elements are often used in sensor appliances with contactless sensing. Electrical characteristics of inductive or capacitive sensor elements may change depending on a physical quantity to be measured and are usually evaluated by means of oscillators, in order to generate an oscillation signal depending on the physical quantity as a sensor signal.

For instance, an inductive sensor element comprises an inductivity such as a coil which is part of an oscillator and which is applied with an electrical oscillation signal. The electrical oscillation results in an alternating magnetic field in the vicinity the inductivity. If an electrically conductive body approaches the inductivity, the alternating magnetic field induces a voltage. This results in eddy currents in the body which themselves generate an interfering magnetic field which overlays the alternating magnetic field. A change of impedance imposed by the interfering magnetic field or an interference of an alternating magnetic field can result in an increase of the attenuation in the oscillator.

A change of attenuation in the oscillator has an effect to generally change the amplitudes of the electrical oscillation which can be detected and analyzed/evaluated. For evaluation, the electrical oscillation signal supplied by the oscillator is conventionally rectified, e.g. by means of a diode, to provide a sensor output which is an electrical direct (DC) quantity, which depends on the absolute value of the change of impedance.

Such inductive sensors are e.g. used as inductive proximity sensors to detect the distance of an electrically conductive object to the sensor. For providing a binary switching signal which is often required in industrial applications, a binary sensor output can be generated from the sensor output by means of a Schmitt-Trigger or comparator.

From document DE 10 2004 034 190 A1 an oscillator circuit for an inductive or capacitive sensor is known. The oscillator circuit comprises a resonant circuit and an operational amplifier, wherein an electrical oscillation of the resonance circuit is tapped at two terminals in a differential manner and is amplified by the operational amplifier.

From document EP 1 183 779 A1 an oscillator for an inductive proximity sensor is known which has a resonant circuit and a comparator. By means of the network with a positive feedback, the output of the comparator is coupled with the non-inverting input of the comparator. Further, the output of the comparator is coupled by means of a negative feedback loop with the inverting input of the comparator and the output of the comparator so that oscillation signals are generated independent from the fact whether power is applied onto the resonant circuit gradually or quickly.

The above documents describe to provide an electrical alternating quantity for evaluation of the oscillation signal obtained by the oscillator. The electrical alternating quantity is usually rectified by means of one or more semiconductor components, such as a diode rectifier or an active rectifier, in order to provide a sensor output representing the physical quantity to be measured, in form of an electrical direct quantity. The use of diode circuits or active rectifiers for rectifying the sensor signal results in a temperature dependency of the evaluation signal which has its disadvantage particularly in application fields with high temperature variations.

Furthermore, evaluating circuits which are based on a diode or rectifier-based rectification of the oscillation signal are usually expensive and have essential power consumption.

SUMMARY OF THE INVENTION

It is an object of the present invention to provide a method and a circuit for evaluating a physical quantity detected by a sensor element which can supply a sensor output as an electrical direct (DC) quantity which is based on an electrical oscillation signal depending on the physical quantity to be measured wherein the sensor output has a low or no temperature dependency. Furthermore, the evaluating circuit shall be implemented with a lower number of components and have lower power consumption.

This object has been achieved by the method for measuring an electrical oscillation quantity depending on a physical quantity to be measured with a sensor element and for providing a sensor output depending on the physical quantity to be measured according to claim 1 and by the evaluating circuit according to the further independent claim.

Further embodiments are indicated in the dependent claims.

According to a first aspect, a method for measuring a physical quantity with a particularly inductive sensor element and for providing a sensor output depending on the physical quantity is provided. The sensor element is part of a resonant circuit whose attenuation depends on the physical quantity being measured. The resonant circuit is excited to generate a periodic oscillation signal, the amplitude of which depends on the attenuation. Further, the oscillation signal is compared with a comparator threshold value in a comparator to produce a periodic comparator signal with a duty cycle depending on the comparator threshold value. The comparator threshold value is set to be different from a mean value of the oscillation signal so that a duty cycle different from 50% is achieved. The sensor output is output as depending on the duty cycle of the comparator signal.

One idea of the above method is basically to analyze an oscillation signal which is provided by an electrical resonant circuit including a sensor element, wherein the amplitude of the oscillation signal depends on the physical quantity to be measured so that a sensor output which depends on the amplitude of the oscillation signal is provided as an electrical direct (DC) voltage or direct (DC) current, respectively.

In common approaches, the oscillation signal of the resonant circuit is amplified and rectified thereafter, e.g. by means of a diode or an active rectifier to obtain the sensor signal. Since semiconductor components usually have a temperature dependency, such an evaluating circuit results in a sensor output which depends on the amplitude of the oscillation signal and also from the temperature of the evaluating circuit. It is maybe disadvantageous particularly in some application fields in which high temperature variations may occur.

The above method facilitates to provide an evaluating circuit with a reduced number of components and particularly without the use of a rectifier for supplying of a temperature-independent sensor output as direct (DC) voltage or direct (DC) current, respectively. The temperature independency is substantially achieved in that the comparator threshold value with respect to which the oscillation signal is evaluated is set, so that it differs from a mean value of the oscillation signal. Thereby, the comparator threshold value determines a switching threshold which is different from the mean value of the oscillation signal or offset/shifted/biased thereto, respectively. Consequently, a periodic comparator signal having a duty cycle not equal to 50% is obtained at an output of the comparator.

Setting of the comparator signal to a duty cycle which is different from 50% is based on the switching threshold set by the comparator threshold value wherein the periodic oscillation signal exceeds or falls below the switching threshold at predetermined time instants. These time instants, however, depend on the slope/gradient of the oscillation signal when the switching threshold differs from the mean value of the oscillation signal. As the slope of the oscillation signal, however, depends on the amplitude of the oscillation signal, the duty cycle depends on the amplitude of the oscillation signal as well when the switching threshold is different from the mean value of the oscillation signal. In other words, the comparator threshold is being set so that the oscillation signal is sampled at a time instant which depends on the amplitude of the oscillation signal.

The sensor output can be obtained by determining an average value of the comparator signal, e.g. by equalizing. As a result, diode or other active semiconductor components which have a significant temperature dependency can be omitted for rectification of the oscillation signal.

Furthermore, the mean value of the oscillation signal can be offset with respect to the comparator threshold value applying a predetermined offset value particularly a predetermined offset voltage wherein the offset value is applied to the oscillation signal or the offset value corresponds to the comparator threshold value or the oscillation signal is set depending on the offset value.

It can be provided that the comparator threshold value is set depending on the duty cycle of the periodic comparator signal.

Particularly, the comparator threshold can be set as the mean value of the periodic comparator signal, particularly obtained by equalizing, wherein the sensor output corresponds to the mean value.

According to an embodiment, an oscillation of the resonant circuit can be maintained by an in-phase feedback of the periodic comparator signal.

The comparator signal can be low-pass filtered wherein an initial build-up of oscillation of the resonant circuit is effected by providing a feedback of the low-pass filtered comparator signal to the comparator threshold value.

According to an embodiment, the comparator threshold value can be offset/shifted depending on the duty cycle of the periodic comparator signal and depending on an predetermined offset value with respect to a mean value of the oscillation signal so that a balanced state between a duty cycle obtained due to the predetermined offset value and a duty cycle obtained depending on the comparator threshold value is obtained.

Hence, a feedback of the output of the comparator is provided whereby the comparator threshold value is set depending on the duty cycle of the comparator signal at the output of the comparator. The dependency can be chosen so that with an increasing deviation of the duty cycle from 50%, the comparator threshold value is increasingly shifted towards the mean value of the oscillation signal. Thereby, at the output of the comparator, a duty cycle of the comparator signal is obtained which is a response on the detuning/offset of the comparator threshold value with respect to a mean value of the oscillation signal and on the amplitude of the oscillation signal. Hence, the comparator threshold value which is a DC voltage can be used as sensor output.

Particularly, the deviation between the predetermined offset value and the comparator threshold value resulting from the duty cycle of the comparator signal result in a balanced state. Thereby, a dependency between the comparator threshold value and the amplitude of the periodic oscillation value is given. The provision of the comparator threshold value as a DC voltage depending on the amplitude of the oscillation signal, allows to omit a rectification of the comparator output signal and to use the comparator threshold value as the provided sensor output.

Furthermore, the sensor output may correspond to a voltage of the comparator threshold value or to an effective voltage obtained by equalizing the periodic comparator signal.

According to a further embodiment, the resonant circuit can be excited in an inversely phased (out-of-phase) manner by applying the periodic comparator signal.

According to a further aspect, an evaluating circuit is provided for measuring a physical quantity with a particularly inductive sensor element and for providing a sensor output depending on the physical quantity to be measured, wherein the evaluating circuit comprises:
  a resonant circuit comprising the sensor element, wherein the resonant circuit has an attenuation which depends on the physical quantity;
  a means for providing an excitation signal for exciting the resonant circuit to produce a periodic oscillation, the amplitude of which depends on the attenuation of the resonant circuit;
  a comparator which is configured to compare the oscillation signal with a comparator threshold value so that a resulting periodic comparator signal is provided which has a duty cycle depending on the comparator threshold value, wherein the sensor output is output as depending on the duty cycle of the comparator signal; and
  a means for shifting/offsetting the comparator threshold value with respect to a mean value of the oscillator signal so that a duty cycle different from 50% is obtained.

Furthermore, an offset voltage source can be provided to offset the mean value of the oscillation signal with respect to the comparator threshold value by means of a predetermined offset value, particularly of a predetermined offset voltage, wherein the offset voltage source is connected so that the offset value is applied to the oscillation signal or that the comparator threshold value corresponds to the offset value or that the oscillation signal is set depending on the offset value.

The means for providing the excitation signal can be provided by a feedback of the comparator signal, particularly by means of a feedback resistance, to the resonant circuit in order to excite the resonant circuit by the periodic comparator signal so that the resonant circuit continuously oscillates, particularly at its resonant frequency.

Particularly, an initial build-up oscillation means can be provided in order to low-pass filter the periodic comparator signal and to provide the comparator threshold value as the low-pass filtered comparator signal or as a signal depending on the low-pass filtered comparator signal so as to allow an initial build-up of the oscillation of the resonant circuit, wherein the low-pass filtered comparator signal is provided as the sensor output.

The sensor element may include an inductivity wherein the resonant circuit comprises the inductivity, whose terminals are coupled with a predetermined potential via resonant circuit capacities, respectively, wherein the feedback of the comparator signal to the resonant circuit is inversely phased (out-of-phase).

BRIEF DESCRIPTION OF THE DRAWINGS

The drawings described herein are for illustrative purposes only of selected embodiments and not all possible implementations, and are not intended to limit the scope of the present disclosure. Embodiments are described in more detail in conjunction with the accompanying drawings, in which.

DETAILED DESCRIPTION OF THE PREFERRED EMBODIMENTS

Example embodiments will now be described more fully with reference to the accompanying drawings.

Figure 1:
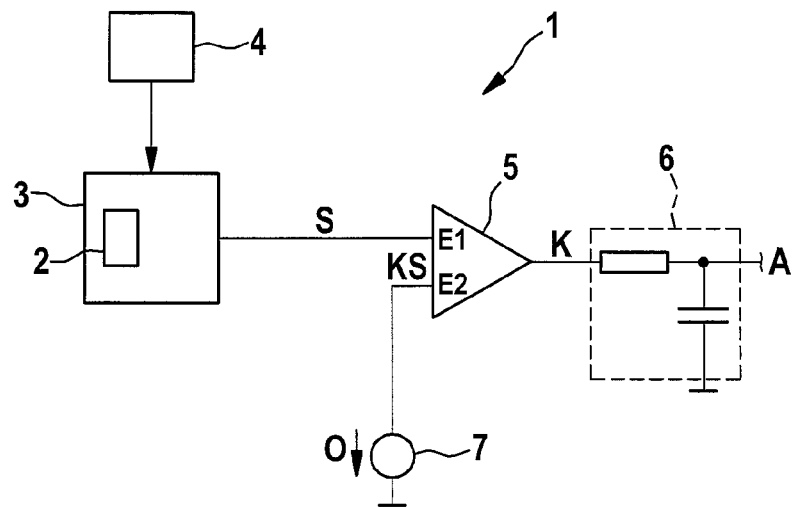
FIG. 1 shows a schematic of an evaluating circuit for a sensor.

FIG. 1 schematically shows an evaluating circuit 1 for a sensor element 2 which is part of a resonant circuit 3 or oscillator, respectively. The sensor element 2 serves to measure a physical quantity and to have a function within the resonant circuit 3 so that a periodic oscillation signal is generated with an amplitude depending on the physical quantity to be measured. For instance, the sensor element 2 can be chosen so that a change of the physical quantity to be measured results in a change of impedance of the sensor element 2. The variation of impedance results in a varying attenuation of the periodic oscillation signal which can be evaluated.

The resonant circuit 3 is continuously excited by means of an excitation means 4 to provide the periodic oscillation signal S. The excitation means 4 serves on one hand to effect an initial build-up of oscillation of the resonant circuit 3 when starting the evaluating circuit 1 and on the other hand to keep up/maintain a continuous oscillation of the resonant circuit 3 by steadily injecting excitation energy. Particularly, the excitation occurs by applying an excitation signal which has a frequency portion/harmonic of a resonance frequency of the resonant circuit 3.

The periodic oscillation signal S is fed to a first input E1 of a comparator 5 and is compared with a predetermined comparator threshold value KS, particularly given as a voltage, at a second input E2. A comparator signal K at an output of the comparator 5 corresponds to a square-wave voltage signal with a periodicity which corresponds to the periodicity of the periodic oscillation signal S.

The comparator threshold value KS can be predetermined by an offset unit 7 which may have the form of an offset voltage source 7 coupled with the second input E2 of the comparator 5.

The offset unit 7 serves to provide the comparator threshold value KS by means of an offset value O and can be given as an offset voltage $U_O$ so that the comparator threshold value KS is shifted/offset with respect to a mean value of the oscillation signal S or is different from the mean value of the oscillation signal S, respectively.

As a mean value, an average value can be applied which may be determined from a maximum and a minimum of the oscillation signal. As a mean value, a value can also be applied which is determined by the integral of the characteristics of the oscillation signal over one period divided by the period time of the oscillation.

The oscillation signal S may substantially correspond to an electrical signal with a close to sinusoidal characteristics wherein a mean value may be determined from the maximum and the minimum of the signal. So, the comparator threshold determined by the comparator threshold value KS with respect to the oscillation signal S, is given as a value between the mean value and the maximum or as a value between the mean value and the minimum value of the oscillation signal S. Therefore, the comparator threshold value KS can be detuned/shifted with respect to the mean value of the oscillation signal S.

The comparator signal K at the output of the comparator 5 is fed to a low-pass filter 6 which e.g. can be implemented as RC element. The low-pass filter 6 serves to equalize the comparator signal K and to supply a sensor output A, particularly as sensor voltage, wherein the sensor output A is an electrical DC quantity proportional to the duty cycle of the comparator signal K.

In case the comparator threshold value KS was set to the mean value of the oscillation signal S, a comparator signal K with a duty cycle of 50% would result at the output of the comparator 5. When offsetting/detuning the comparator threshold value KS with respect to the mean value of the oscillation signal S, a duty cycle of the comparator signal K results which differs/deviates from 50% as the switching threshold of the comparator 5 crosses the sinusoidal characteristics of the oscillation signal S at time instants which are different from the time instants at zero crossing.

Figure 2:
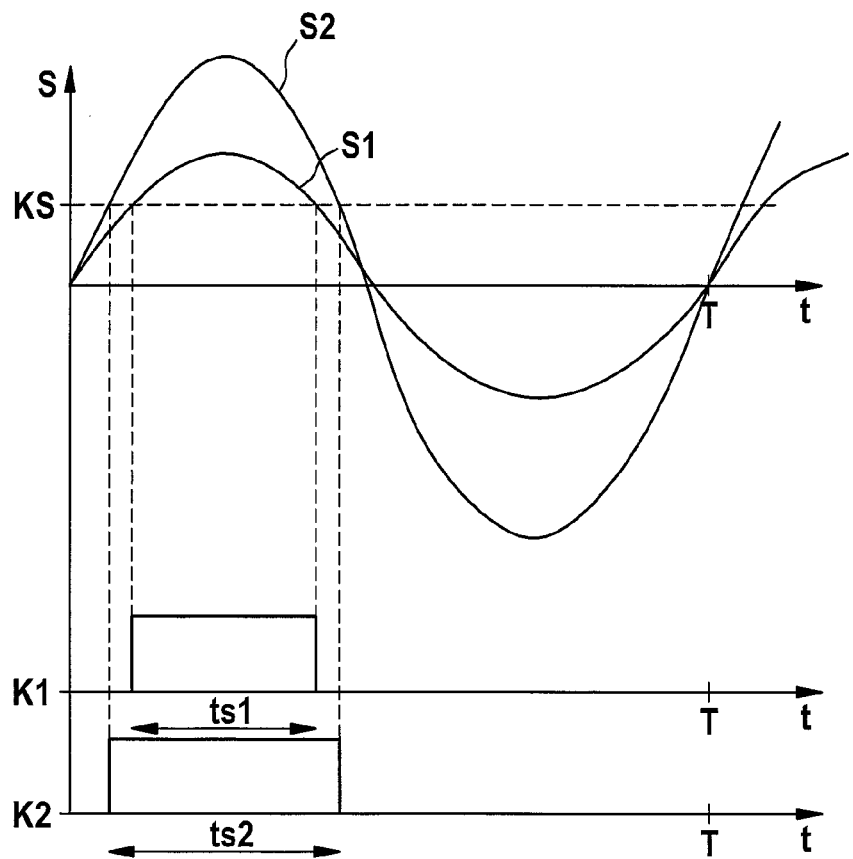
FIG. 2 shows a characteristics of two exemplary oscillation signals with different amplitudes and the comparator signals resulting thereof.

The duty cycle which is a result of the detuning of the comparator threshold value KS from the mean value of the oscillation signal S, depends on one hand on the absolute value of the comparator threshold value KS or on its difference to the mean value of the oscillation signal S, respectively, and on the other hand depends on the amplitude of the oscillation signal S. As can be seen in the characteristics shown in FIG. 2 showing two exemplary sinusoidal oscillation signals S1, S2 with different amplitudes, the resulting duty cycles of the comparator signals K1, K2 arise from the different slopes of the oscillation signal S at time instants determined by the switching thresholds defined by the respective comparator threshold value KS. So the duty cycle ts1/T of the resulting first comparator signal K1 at a period T related to a first oscillation signal S1 with a lower amplitude is lower than the duty cycle ts2/T of the resulting second comparator signal K2 related to the second oscillation signal S2 with a higher amplitude, wherein ts1 and ts2 correspond to the time durations in which the respective oscillation signal S, S1, S2 has a higher value than is determined by the comparator threshold value KS.

In alternative embodiments, the offset value O can also be applied on the oscillation signal S in that the offset unit 7 is arranged in the signal path of the resonant circuit 3. Thereby, the offset value O is added to the oscillation signal S. At the second input E2 of the comparator 5, a predetermined comparison value is applied only, e.g. in form of a predetermined voltage potential. Of course, the operational range of the comparator 5 needs to be considered for dimensioning of the offset value O, the comparison value and of the resonant circuit 3.

Figure 3:
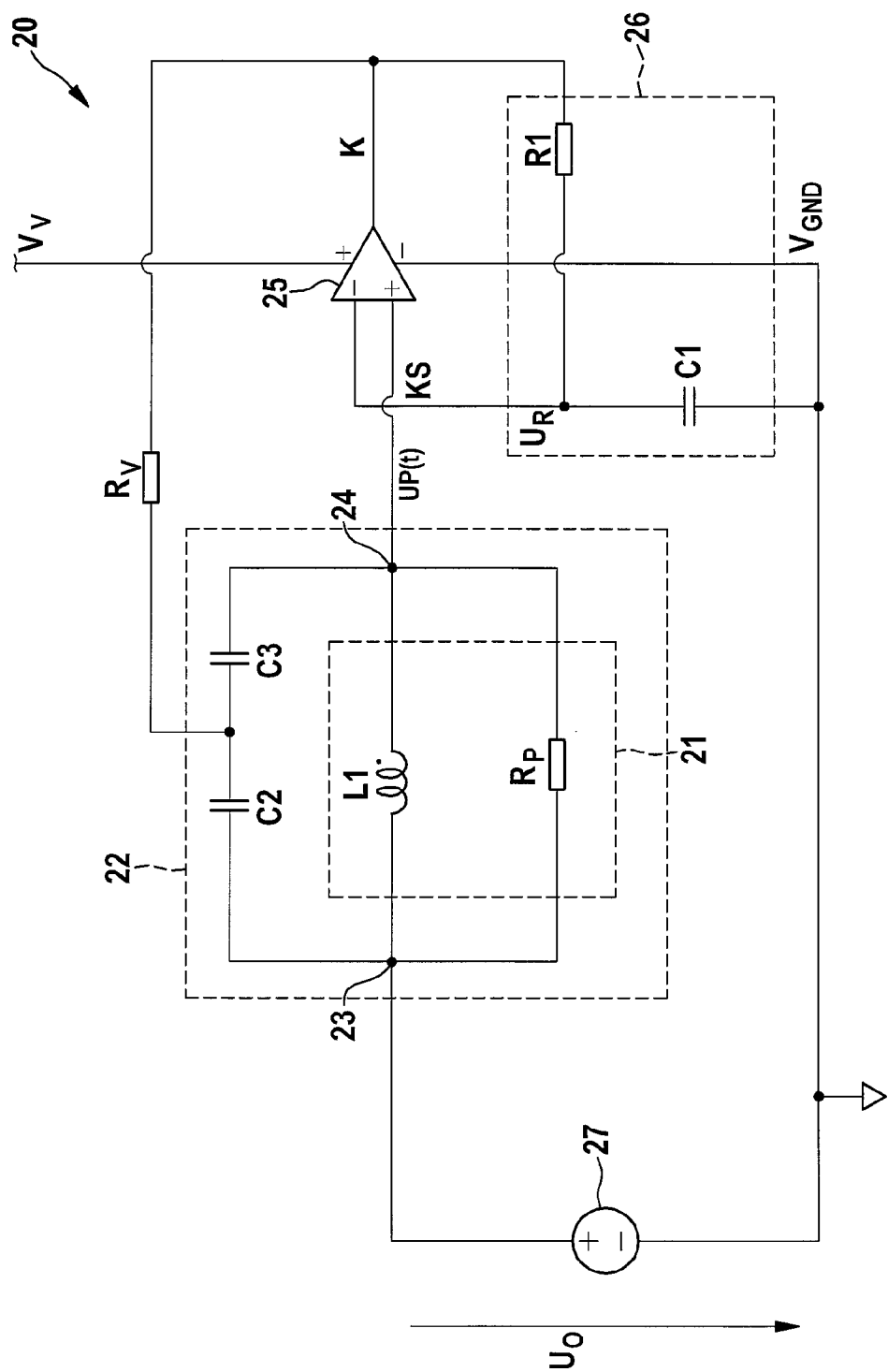
FIG. 3 shows an embodiment of the evaluating circuit for an inductive sensor.

In FIG. 3, a concrete schematic of an evaluating circuit 20 applying an inductive sensor is shown as an example for the evaluating circuit 1. The inductive sensor comprises a sensor element 21 which is represented as inductivity L1 in the shown schematic. The inductivity L1 is parallel to two serially connected resonant circuit capacities C2 and C3 to form a resonant circuit 22. An oscillation of the resonant circuit 22 results in an alternating current in the inductivity L1 implemented as a coil wherein an alternating magnetic field is generated.

When the inductive sensor is applied in an inductive proximity sensor, it can be detected whether an object including an electrically conductive element changes its position in the alternating magnetic field or enters the alternating field by approaching the inductive sensor. This causes the generation of eddy currents in the electrically conductive elements which interfere with the alternating magnetic field and cause interferences in the generated alternating magnetic field. This interference of the alternating magnetic field has an effect of a changed impedance of the sensor element 21 or of a changed attenuation of the oscillation in the resonant circuit 22, respectively. The electrical effect of this attenuation is represented by the resistance $R_P$ shown as parallely coupled to the inductivity L1 in the resonant circuit 22.

The resonant circuit 22 is implemented as a parallel resonant circuit and has a first terminal 23, onto which a predetermined offset voltage $U_O$ of a corresponding offset voltage source 27 is applied, and a second terminal 24 which is coupled with a non-inverting input of the comparator 25. The comparator 25 can e.g. be implemented as a differential amplifier or an operational amplifier. Hence, a voltage is applied at the non-inverting input of the comparator 25 wherein the voltage corresponds to a sum of the offset voltage $U_O$ and a resonant circuit voltage which corresponds to the oscillation signal S.

The comparator 25 is supplied with electrical energy by a supply voltage $U_V$, i.e. the voltage between a high supply potential $V_V$ and a low supply potential $V_{GND}$, particularly a ground potential. The comparator 25 is preferably implemented as a rail-to-rail comparator, i.e. the high supply potential $V_V$ is output for a positive comparison result and the low supply potential $V_{GND}$ is output for a negative comparison result at the comparator output corresponding to a comparator signal K which preferably corresponds to a voltage signal.

The comparator signal K is coupled via a feedback resistance $R_V$ to a node between the two resonant circuit capacities C2 and C3 in order to provide a permanent excitation for the resonant circuit 22 so that a constant oscillation at a resonant frequency of the resonant circuit 22 is achieved. This occurs as the comparator signal K which is a square-wave signal has a period which corresponds to the period of the oscillation signal S. Hence, the comparator signal K has, at a duty cycle different from 50%, a frequency portion which is sufficient for the mainly in-phase excitation of the resonant circuit 22 via the feedback of the feedback resistance $R_V$. Of course, it is also possible to excite the resonant circuit 22 and to maintain the oscillation by means of a separate excitation means 4 which is independent from the comparator signal K.

The comparator signal K which substantially corresponds to a square-wave signal with a duty cycle and with signal levels which correspond to the high supply potential $V_V$ and the low supply potential $V_{GND}$, is fed back via a low-pass filter 26 to an inverting input of the comparator 25. The low-pass filter 26 comprises a filter resistance R1 and a filter capacity C1 which are serially connected so that a reference voltage $U_R$ at a node between the filter resistance R1 and the filter capacity C1 is obtained wherein the reference voltage $U_R$ is applied onto the inverting input of the comparators 25 as comparator threshold value KS or comparator threshold voltage, respectively.

The so formed low-pass filter 26 is configured so that when starting up (powering up) the evaluating circuit 20, the reference voltage $U_R$ at the inverting input of the comparator 25 has an oscillation which is of high amplitude directly after the start-up and having a decreasing amplitude thereafter. The high waviness of the reference voltage $U_R$ at start-up leads to an alternating signal level of the comparator signal K which is coupled into the node between the two resonant circuit capacities C2 and C3 via the feedback resistance $R_V$. Thereby, the feedback onto the inverting input of the comparator 25 supports the building up of oscillation by initially generating a comparator signal K with periodically alternating signal levels until the resonant circuit 22 has started oscillation based on the feedback through the feedback resistance $R_V$.

In a steady state, the low-pass filter 26 further supplies the reference voltage $U_R$ at the inverting input of the comparator 25 which is substantially provided as DC voltage by equalization of the comparator signal K.

Substantially, as the reference voltage $U_R$ a voltage is obtained which is generated by the duty cycle of the comparator signal K determined by the steady state of the resonant circuit 22 as well as by the high voltage potential $V_V$ and the low supply potential $V_{GND}$. The reference voltage $U_R$ is produced by the comparator 25 and the potentials of the high and low levels of the supply potential as well as by the low-pass filter 26 so that a voltage which depends on the duty cycle of the comparator signal K, is applied at the inverting input of the comparator 25. In the present embodiment, a reference voltage $U_R$ corresponds to half of the supply voltage $U_V/2$ at a duty cycle of 50%.

Substantially, the oscillation signal generated in the resonant circuit 22 has sinusoidal characteristics, the mean value of which is determined by the offset voltage $U_O$. If the evaluating circuit 20 is tuned, i.e. the offset voltage $U_O$ corresponds to the reference voltage $U_R$, the output of the comparator 25 shows a signal with a duty cycle of 50% as comparator signal K. The evaluating circuit 20, however, is detuned if the reference voltage $U_R$ resulting from the duty cycle of the comparator signal K corresponds to a voltage level different from the offset voltage $U_O$. The detuning has an effect that the oscillation signal up(t) onto which the offset voltage $U_O$ is applied, is not sampled with a comparator threshold value KS which corresponds to the mean value of the oscillation signal up(t) and that a comparator signal K is produced at the output of the comparator 25, whose duty cycle differs/deviates from the duty cycle of 50%. So the reference voltage $U_R$ changes and a balanced state is achieved in which the resulting duty cycle of the comparator signal K causes a reference voltage $U_R$ which differs from the mean value of the oscillation so that as a comparator signal K a signal with the corresponding duty cycle is obtained.

Figure 4:
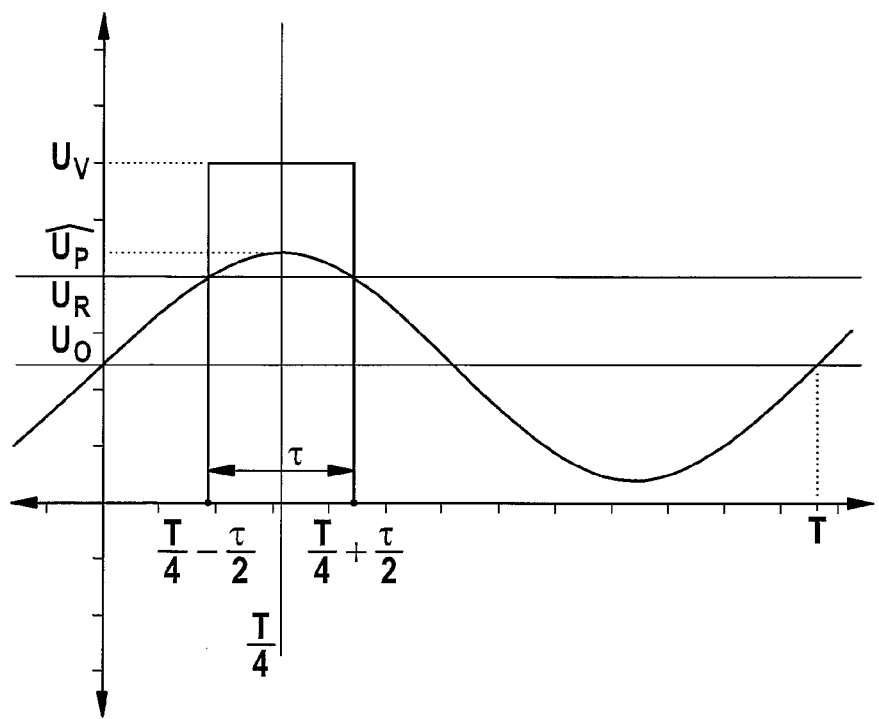
FIG. 4 schematically shows a time characteristics of the oscillation signal as an idealized sinusoidal signal.

In FIG. 4, the time characteristics of the oscillation signal S for the evaluating circuit 20 of FIG. 3 is shown as an idealized sinusoidal signal. It holds:

$$U_a = \widetilde{U_p} - U_o$$

$$up(t) = U_o + U_a \sin(\omega t)$$

wherein $U_a$ corresponds to the amplitude of the oscillation, $\widetilde{U_p}$ to the maximum signal value of the oscillation signal S and up(t) to the oscillation signal S. Furthermore, it holds due to the feedback through the low-pass filter 26 in steady state:

$$U_R = \frac{\tau}{T} U v$$

$$t_1 = \frac{T}{4} - \frac{\tau}{2}$$

It follows:

$$\frac{\tau}{T} = \frac{1}{2} - \frac{1}{\pi}\arcsin\left(\frac{\frac{\tau}{T}Uv - Uo}{U_a}\right) \approx \frac{1}{2} - \frac{1}{\pi}\left(\frac{\frac{\tau}{T}Uv - Uo}{U_a}\right)$$

and so $$U_R \approx \frac{1}{2} - \frac{1}{\pi}\left(\frac{\frac{\tau}{T}Uv - Uo}{U_a}\right) Uv$$

and consequently:

$$\frac{\tau}{T} = \frac{\pi U_a + 2Uo}{2(\pi U_a + Uv)}$$

Figure 5:
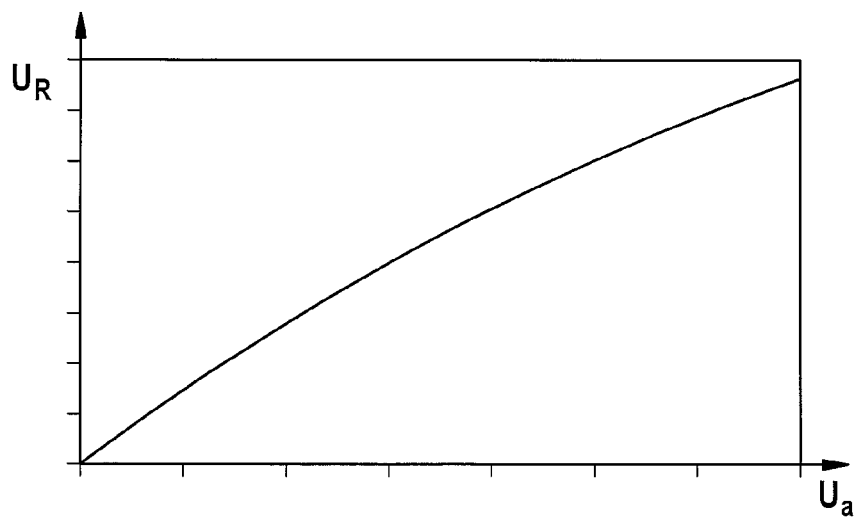
FIG. 5 schematically shows a close to linear dependency between the amplitude of the oscillation signal and the output quantity.

It is obtained a characteristics of the reference voltage $U_R$ as sensor signal or sensor output A, respectively, over the amplitude $U_a$ of the oscillation signal S or up(t), respectively, as it is shown in FIG. 5. It can be seen that the sensor output A, i.e. the reference voltage $U_R$, substantially corresponds to a DC voltage which is linear to the amplitude $U_a$ of the oscillation signal up(t). So the evaluating circuit 20 is suitable to take the reference voltage $U_R$ as a representing sensor output A for the amplitude $U_a$ of the oscillation signal S or for a physical quantity to be measured and which is reflected in the amplitude $U_a$ of the oscillation signal S. The reference voltage $U_R$ is provided as DC voltage and no further rectification is therefore needed.

As the comparator 25 can be implemented as the only active electronic component of the evaluating circuit 20, preferably as a rail-to-rail comparator, a temperature-dependency of the evaluating circuit 20 with respect to the output quantity (sensor output) is low and particularly limited to only the switching threshold of the comparator 25.

Substantially, the feedback coupling of the comparator output to the inverting input of the comparator 25 is provided to initiate an excitation of the resonant circuit 22 so that the oscillation of the resonant circuit 22 can be maintained by the feedback of the comparator output. However, as the comparator output is fed back to the inverting input of the comparator 25 by means of the low-pass filter 26, the low-pass filter 26 can also be used for supplying the sensor output A. In other words, the reference voltage $U_R$ corresponds to the sensor output A, whose potential depends on the amplitude $U_a$ of the oscillation signal S. Therefore, any means subsequently coupled to the comparator 25, such as a further low-pass filter, a rectifier, or the like, can be omitted and the reference voltage $U_R$ can be applied as sensor output A instead. Consequently, an evaluating circuit 20 is provided which can be operated without passive or active rectification so that the number of required components and the total power consumption is reduced.

Figure 6:
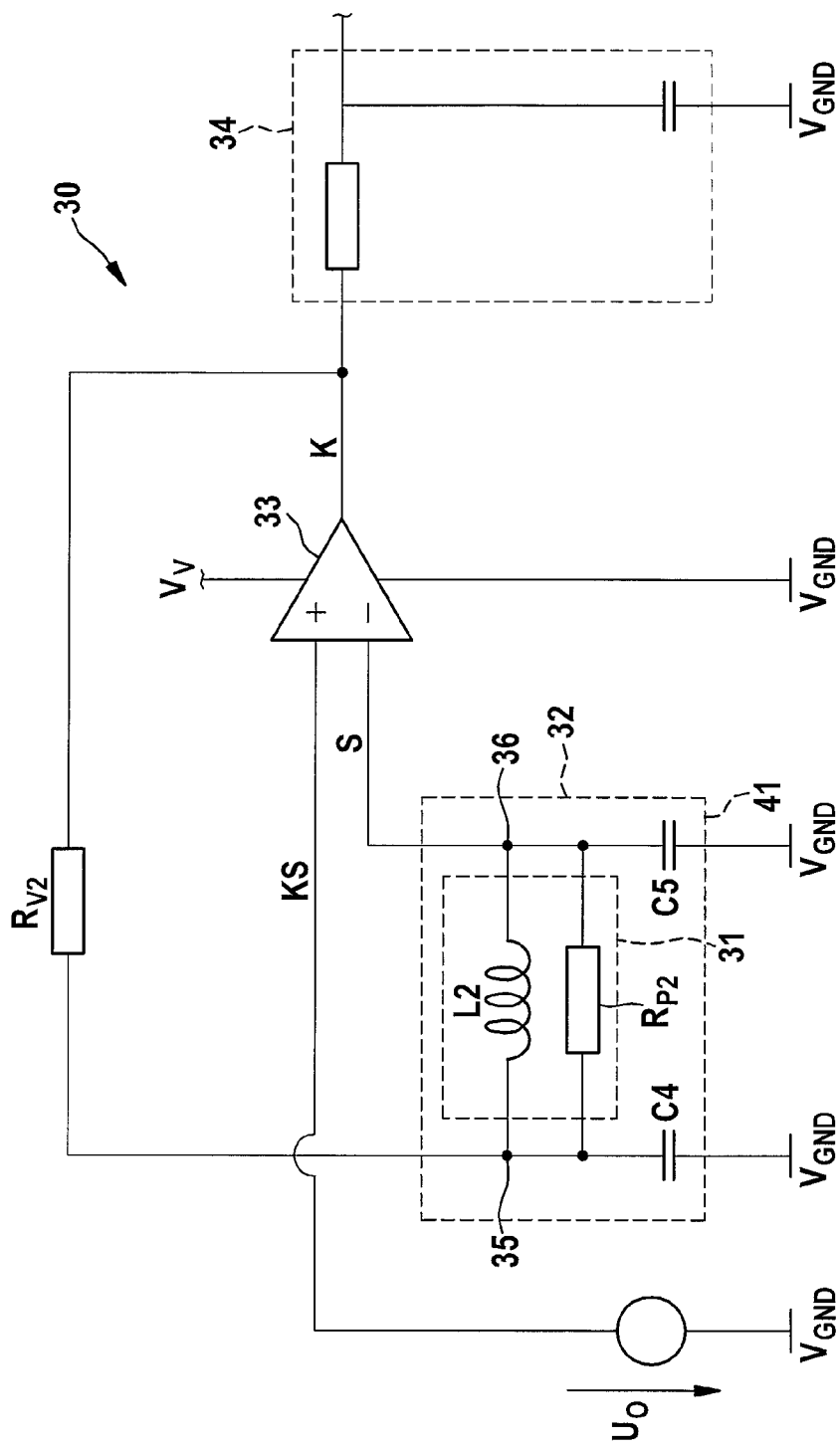
FIG. 6 shows a schematic of the evaluating circuit for an inductive sensor according to a further embodiment.

FIG. 6 shows a schematic of a further with respect to the evaluating circuit 1 more concrete embodiment of an evaluating circuit 30 for an inductive sensor with a sensor element 31 comprising inductivity L2 which forms a resonant circuit 32 with a first and a second resonant circuit capacity C4, C5. The resonant circuit 32 is formed by a circuitry in which a first terminal 35 of the inductivity L2 is connected through the first resonant circuit capacity C4 with a low supply potential $V_{GND}$, particularly a ground potential, and a second terminal 36 of the inductivity L2 is connected through the second resonant circuit capacity C5 with the low supply potential $V_{GND}$. Interferences in the alternating magnetic field of the inductivity L2, which is formed as a coil, results in a variation of impedance or in an attenuation of an oscillation of the resonant circuit 32 which is reflected by the resistance $R_{P2}$ connected in parallel to the inductivity L2 according to the schematic.

The second terminal 36 of the inductivity L2 provides the oscillation signal S at an inverting input of the comparator 33. So the resonant circuit 32 can be excited through a feedback resistance $R_{V2}$ via the first terminal 35 of the inductivity L2 at least mainly in an inversely manner or in an out-of-phase manner. The predetermined offset voltage $U_O$ is applied as the comparator threshold value KS at the non-inverting input of the comparator 33.

The feedback resistance $R_{V2}$ serves to start up oscillation of the resonant circuit 32 in conjunction with the first resonant circuit capacity C4. So the feedback resistance $R_{V2}$ and the resonant circuit capacities C4, C5 form/act as the low-pass filter 26 and the feedback resistance $R_{V2}$ also has the task to maintain the oscillation of the resonance circuit 32 as does the feedback resistance $R_V$ of one of the embodiments described above.

Particularly, all signal-carrying nodes in the evaluating circuit 30 of the embodiment of FIG. 6 are capacitively connected with the low supply potential $V_{GND}$ due to the coupling of the resonant circuit capacities C4 and C5. So the construction of the resonant circuit 32 and its out-of-phase excitation allows an implementation of the evaluating circuit 30 by which interferences onto the evaluating circuit 30 can be substantially reduced.

The operation principle of the embodiment of FIG. 6 corresponds to the one of the embodiments described above. By means of the offset voltage $U_O$, a comparator threshold value KS is given by which the circuit can be detuned. So a duty cycle different from 50% is obtained at the comparator output which results from the offset voltage $U_O$ and the voltage level of the mean value of the oscillation signal S.

For providing the sensor output A, a low-pass filter 34 subsequently coupled to the comparator 33 implemented as an RC-element is provided which has an intermediate node at which the sensor output A can be tapped as a DC voltage.

What is claimed is:

1. A method for measuring a physical quantity with a, particularly inductive, sensor element and for providing a sensor output depending on the physical quantity,
   wherein the sensor element is part of a resonant circuit whose attenuation depends on the physical quantity being measured,
   wherein the resonant circuit is excited to generate a periodic oscillation signal having a mean amplitude value, the amplitude of which depends on the attenuation,
   wherein the oscillation signal is compared with a comparator threshold value in a comparator to produce a periodic comparator signal with a duty cycle depending on the comparator threshold value,
   setting the comparator threshold value to be different than the mean amplitude value, wherein in steady state the duty cycle is different from 50% and wherein the sensor output depends on the duty cycle of the comparator signal.

2. The method according to claim 1, wherein the mean value of the oscillation signal is offset with respect to the comparator threshold value applying a predetermined offset value, particularly a predetermined offset voltage, wherein the offset value is applied to the oscillation signal or the offset value corresponds to the comparator threshold value or the oscillation signal is set depending on the offset value.

3. The method according to claim 1, wherein the comparator threshold value is set depending on the duty cycle of the periodic comparator signal.

4. The method according to claim 3, wherein the comparator threshold value is set as the mean value of the periodic comparator signal, particularly obtained by equalizing, wherein the sensor output corresponds to the mean value.

5. The method according to claim 1, wherein an oscillation of the resonant circuit is maintained by an in-phase feedback of the periodic comparator signal.

6. The method according to claim 1, wherein the comparator signal is low-pass filtered wherein an initial build-up of oscillation of the resonant circuit is effected by providing a feedback of the low-pass filtered comparator signal onto the comparator threshold value.

7. The method according to claim 1, wherein the comparator threshold value is changed depending on the duty cycle of the periodic comparator signal and depending on an predetermined offset value with respect to a mean value of the oscillation signal so that a balanced state between a duty cycle obtained due to the predetermined offset value and a duty cycle obtained depending on the comparator threshold value is obtained.

8. The method according to claim 1, wherein the sensor output corresponds to a voltage of the comparator threshold value or to an effective voltage obtained by equalizing the periodic comparator signal.

9. The method according to claim 1, wherein the resonant circuit is excited in an inversely phased (out-of-phase) manner by applying the periodic comparator signal.

10. An evaluating circuit for measuring a physical quantity with a, particularly inductive, sensor element and for providing a sensor output depending on the physical quantity to be measured, wherein the evaluating circuit comprises:
    a resonant circuit comprising the sensor element, wherein the resonant circuit has an attenuation which depends on the physical quantity;
    a means for providing an excitation signal for exciting the resonant circuit to produce a periodic oscillation signal having a mean amplitude value, whose amplitude depends on the attenuation of the resonant circuit;
    a comparator which is configured to compare the periodic oscillation signal with a comparator threshold value so that a resulting periodic comparator signal is provided which has a duty cycle depending on the comparator threshold value, wherein the sensor output is output as depending on the duty cycle of the comparator signal; and
    a means for changing the comparator threshold value to be different than the mean amplitude value, wherein in the steady state the duty cycle is different than 50%.

11. The evaluating circuit according to claim 10, wherein an offset voltage source can be provided to offset the mean value of the oscillation signal with respect to the comparator threshold value by means of a predetermined offset value, particularly of a predetermined offset voltage, wherein the offset voltage source is connected so that the offset value is applied to the oscillation signal or that the comparator threshold value corresponds to the offset value or that the oscillation signal is set depending on the offset value.

12. The evaluating circuit according to claim 10, wherein the means for providing the excitation signal provides a feedback of the comparator signal, particularly by means of a feedback resistance, to the resonant circuit in order to excite the resonant circuit by the periodic comparator signal so that the resonant circuit continuously oscillates, particularly at its resonant frequency.

13. The evaluating circuit according to claim 12, wherein an initial build-up oscillation means is provided in order to low-pass filter the periodic comparator signal and to provide the comparator threshold value as the low-pass filtered comparator signal or as a signal depending on the low-pass filtered comparator signal so as to allow an initial build-up of the oscillation of the resonant circuit, wherein the low-pass filtered comparator signal is provided as the sensor output.

14. The evaluating circuit according to claim 12, wherein the sensor element includes an inductivity wherein the resonant circuit comprises the inductivity, whose terminals are coupled with a predetermined potential via resonant circuit capacities, respectively, wherein the feedback of the comparator signal to the resonant circuit is out-of-phase.

* * * * *